United States Patent [19]

Dionne

[11] Patent Number: 5,538,975
[45] Date of Patent: Jul. 23, 1996

[54] 1,3-OXATHIOLANE NUCLEOSIDE COMPOUNDS AND COMPOSITIONS

[75] Inventor: Gervais Dionne, Laval, Canada

[73] Assignee: BioChem Pharma, Inc., Laval, Canada

[21] Appl. No.: 190,203

[22] PCT Filed: Jul. 24, 1992

[86] PCT No.: PCT/CA92/00321

§ 371 Date: Feb. 1, 1994

§ 102(e) Date: Feb. 1, 1994

[87] PCT Pub. No.: WO93/03027

PCT Pub. Date: Feb. 18, 1993

[30] Foreign Application Priority Data

Aug. 1, 1991 [GB] United Kingdom .................. 9116601

[51] Int. Cl.$^6$ .................. C07D 411/04; A61K 31/505
[52] U.S. Cl. .................. 514/256; 514/49; 514/50; 514/269; 514/274; 536/4.1; 544/242
[58] Field of Search .................. 536/4.1; 514/23, 514/24, 49, 274, 85, 256, 269; 544/242

[56] References Cited

U.S. PATENT DOCUMENTS

| | | | |
|---|---|---|---|
| 4,366,381 | 6/1982 | Nagata et al. | 544/313 |
| 5,047,407 | 9/1991 | Belleau et al. | 514/274 |
| 5,204,466 | 4/1993 | Liotta et al. | 544/317 |
| 5,210,085 | 5/1993 | Liotta et al. | 514/274 |
| 5,248,776 | 9/1993 | Chu et al. | 544/310 |
| 5,270,315 | 12/1993 | Belleau et al. | 514/262 |
| 5,276,151 | 1/1994 | Liotta | 544/317 |
| 5,444,063 | 8/1995 | Schinazi | 514/262 |
| 5,466,806 | 11/1995 | Belleau et al. | 544/310 |

FOREIGN PATENT DOCUMENTS

| | | |
|---|---|---|
| 0382526 | 8/1990 | European Pat. Off. . |
| WO91/11186 | 8/1991 | WIPO .................. 514/274 |
| WO91/17159 | 11/1991 | WIPO .................. 514/274 |
| WO92/10496 | 6/1992 | WIPO .................. 514/274 |
| WO92/14743 | 9/1992 | WIPO .................. 514/274 |
| WO92/15308 | 9/1992 | WIPO .................. 514/274 |
| WO92/15309 | 9/1992 | WIPO .................. 514/274 |
| WO92/18517 | 10/1992 | WIPO .................. 514/274 |
| 9221676 | 12/1992 | WIPO . |
| WO93/03027 | 2/1993 | WIPO .................. 514/274 |
| 9414802 | 7/1994 | WIPO . |

OTHER PUBLICATIONS

Doong, et al. "Inhibition of the Replication of Hepatitis B Virus In Vitro by 2',3'-Dixeoxy-3'-Thiacytidine and Related Analogues", *Proc. Natl. Acad. Sci U.S.A.*, vol. 88(19), pp. 8495–8499 (1991).

Jeong, et al. "Structure–Activity Relationships of β-D-(2S, 5R)- and α-D-(2S,5R)-1,3-Oxathiolanyl Nucleosides as Potential Anti–HIV Agents", *J. Med. Chem.*, vol. 36, pp. 2627–2638 (1993).

Jeong et al., "Asymmetric Synthesis and Biological Evaluation of β-L-(2R,5S)- and α-L-(2R,5R)-1,3-Oxathiolane-Pyrimidine and -Purine Nucleosides as Potential Anti–HIV Agents", *J. Med. Chem.*, vol. 36(2) pp. 181–195 (1993).

Frick, et al., "Pharmacokinetics, Oral Bioavailability, and Metabolic Disposition in Rats of (–)-cis-5-Fluoro-1-[2-(Hydroxymethyl)-1,3-Oxathiolan-5-yl]Cytosine, a Nucleoside Analog Active Against Human Immunodeficiency Virus and Hepatitis B Virus", *Antimicrob. Agents & Chemother.*, vol. 37(11), pp. 2285–2292 (1993).

Furman, et al., "The Anti–Hepatitis B Virus Activities, Cytotoxicities, and Anabolic Profiles of the (–) and (+) Enantiomers of cis-5-Fluoro-1-[2-(Hydroxymethyl)-1, 3-Oxathiolan-5-yl]Cytosine", *Antimicrob. Agents & Chemother.*, vol. 36(12), pp. 2686–2692 (1992).

Chang et al., *J. of Biol. Chemistry*, vol. 267, No. 31, pp. 22414–22420, Nov. 5, 1992.

Primary Examiner—James O. Wilson
Attorney, Agent, or Firm—Fish & Neave; James F. Haley, Jr.; Leslie A. McDonell

[57] ABSTRACT

The invention relates to 1,3-oxathiolane nucleoside analogues and their use in the treatment of viral infections. More specifically, this invention relates to (–)-4-amino-5-fluoro-1-(2-hydroxymethyl-1,3-oxathiolan-5-yl)-(1H)-pyrimidin-2-one and pharmaceutically acceptable derivatives and pharmaceutical formulations thereof.

5 Claims, No Drawings

1,3-OXATHIOLANE NUCLEOSIDE COMPOUNDS AND COMPOSITIONS

The present invention relates to nucleoside analogues and their use in medicine. More specifically the invention is concerned with 1,3-oxathiolane nucleoside analogues, pharmaceutical formulations thereof and the use thereof in the treatment of viral infections.

The only compound currently approved for the treatment of conditions caused by HIV is 3'-azido-3'-deoxythymidine (AZT, zidovudine, BW 509U). However, this compound has a significant side-effect liability and thus either cannot be employed or, once employed, may have to be withdrawn in a significant number of patients. There is in consequence a continuing need to provide compounds which are effective against HIV but with a concommitant significantly better therapeutic index.

The compound of formula (I)

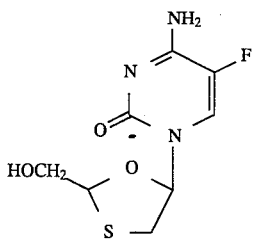

is a racemic mixture of the two enantiomers of formulae (I-1) and (I-2):

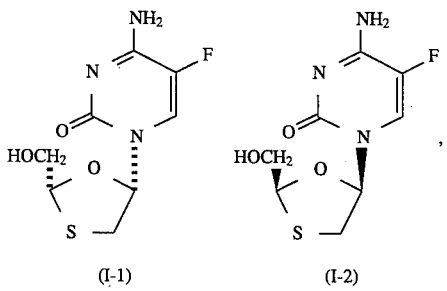

We have now found that, surprisingly, the (−)-enantiomer of the compound of formula (I) is much more active than the (+)-enantiomer, although both enantiomers show unexpectedly low cytotoxicity. There is thus provided in a first aspect of the invention the (−)(or laevorotatory) enantiomer of the compound of formula (I) and phazmaceutically acceptable derivatives thereof.

The (−)-enantiomer has the chemical name (−)-4-amino-5-fluoro-1-(2-hydroxymethyl-1,3-oxathiolan-5-yl)-(1H)-pyrimidin-2-one (hereinafter compound (A)). This enantiomer has the absolute stereochemistry shown in formula (I-1).

Preferably compound (A) is provided substantially free of the corresponding (+)-enantiomer, that is to say no more than about 5% w/w of the (+)-enantiomer, more preferably no more than about 2%, and most preferably less than about 1% w/w is present.

By "a pharmaceutically acceptable derivative" is meant any pharmaceutically acceptable salt, ester, or salt of such ester, of compound (A) or any other compound which, upon administration to the recipient, is capable of providing (directly or indirectly) compound (A) or an antivirally active metabolite or residue thereof.

It will be appreciated by those skilled in the art that compound (A) may be modified to provide pharmaceutically acceptable derivatives thereof, at functional groups in both the base moiety and at the hydroxymethyl group of the oxathiolane ring. Modification at all such functional groups are included within the scope of the invention. However, of particular interest are pharmaceutically acceptable derivatives obtained by modification of the 2-hydroxymethyl group of the oxathiolane ring.

Preferred esters of compound (A) include the compounds in which the hydrogen of the 2-hydroxymethyl group is replaced by an acyl function

in which the non-carbonyl moiety R of the ester is selected from hydrogen, straight or branched chain alkyl (e.g., methyl, ethyl, n-propyl, t-butyl, n-butyl), alkoxyalkyl (e.g., methoxymethylL), aralkyl (e.g., benzyl), aryloxyalkyl (e.g., phenoxymethyl), aryl (e.g., phenyl optionally substituted by halogen, $C_{1-4}$ alkyl or $C_{1-4}$ alkoxy); sulphonate esters such as alkyl- or aralkylsulphonyl (e.g., methanesulphonyl); amino acid esters (e.g., L-valyl or L-isoleucyl) and mono-, di- or tri-phosphate esters.

With regard to the above described esters, unless otherwise specified, any alkyl moiety present advantageously contains 1 to 16 carbon atoms, particularly 1 to 4 carbon atoms. Any aryl moiety present in such esters advantageously comprises a phenyl group.

In particular the esters may be a $C_{1-16}$ alkyl ester, an unsubstituted benzyl ester or a benzyl ester substituted by at least one halogen (bromine, chlorine, fluorine or iodine), $C_{1-6}$ alkyl, $C_{1-6}$ alkoxy, nitro or trifluoromethyl groups.

Pharmaceutically acceptable salts of the compound (A) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and $NR_4^+$ (where R is $C_{1-4}$ alkyl) salts.

References hereinafter to a compound according to the invention include both the compound (A) and its pharmaceutically acceptable derivatives.

The compounds of the invention either themselves possess antiviral activity and/or are metabolizable to such compounds. In particular these compounds are effective in inhibiting the replication of retroviruses, including human retroviruses such as human immunodeficiency viruses (HIV's), the causative agents of AIDS.

The compounds of the invention are also useful in the treatment of animals including man infected with the hepatitis B virus (HBV).

There is thus provided as a further aspect of the invention compound (A) or a pharmaceutically acceptable derivative thereof for use as an active therapeutic agent in particular as an antiviral agent, for example in the treatment of retroviral infections or HBV infections.

In a further or alternative aspect there is provided a method for the treatment of a vital infection, in particular an infection caused by HBV or a retrovirus such as HIV, in a mammal including man comprising administration of an effective Mount of compound (A) or a pharmaceutically acceptable derivative thereof.

There is also provided in a further or alternative aspect use of compound (A) or a pharmaceutically acceptable derivative thereof for the manufacture of a medicament for the treatment of a viral infection.

The compounds of the invention are also useful in the treatment of AIDS related conditions such as AIDS-related complex (ARC), progressive generalized lymphadenopathy (PGL), AIDS-related neurological conditions (such a dementia or tropical paraparesis), anti-HIV antibody positive and HIV-positive conditions. Kaposi's sarcoma, thrombocytopenia purpurea and associated opportunistic infections for example *pneumocystis carinii*.

The compounds of the invention are also useful in the prevention of progression to clinical illness of individuals who are anti-HIV antibody or HIV-antigen positive and in prophylaxis following exposure to HIV.

The compound (A) or pharmaceutically acceptable derivatives thereof may also be used for the prevention of viral contamination of physiological fluids such as blood or semen in vitro.

The compounds of the invention are also useful in the treatment of animals including man infected with the hepatitis B virus.

It will be appreciated by those skilled in the art that reference herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient and will be ultimately at the discretion of the attendant physician or veterinarian. In general however a suitable dose will be in the range of from about 0.1 to about 750 mg/kg of body-weight per day preferably in the range of 0.5 to 60 mg/kg/day, most preferably in the range of 1 to 20 mg/kg/day.

The desired dose may conveniently be presented in a single dose or as divided doses administered at appropriate intervals, for example as two, three, four or more sub-doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 µM, preferably about 2 to 50 µM, most preferably about 3 to about 30 µM. This may be achieved, for example, by the intravenous injection of a 0.1 to 5% solution of the active ingredient, optionally in saline, or orally administered as a boltus containing about 1 to about 100 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation.

The invention thus further provides a pharmaceutically formulation comprising compound (A) or a pharmaceutically acceptable derivative thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tables each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation or sterile solid or by lyophilization from solution, for constitution with a suitable vehicle, e.g., sterile, pyrogen-free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops.

Drops may be formulated with an aqueous or non-aqueous base also comprising one or more dispersing agents, solubilizing agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g., gelatin or blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial agents, or preservatives.

The compounds of the invention may also be used in combination with other therapeutic agents for example other antiinfective agents. In particular the compounds of the invention may be employed together with known antiviral agents.

The invention thus provides, in a further aspect, a combination comprising the compound (A) or a physiologically acceptable derivative thereof together with another therapeutically active agent, in particular an antiviral agent.

The combinations referred to above may conveniently be presented for use in the form of a pharmaceutical formulation and thus pharmaceutical formulations comprising a combination as defined above together with a phazmaceutically acceptable carrier therefor comprise a further aspect of the invention.

Suitable therapeutic agents for use in such combinations include acyclic nucleosides such as acyclovir or ganciclovir, interferons such as alpha, beta or gamma-interferon, renal excretion inhibitors such as probenecid, nucleoside transport inhibitors such as dipyridamole, 2',3'-dideoxynucleosides such as AZT, 2',3'-dideoxycytidine, 2',3'-dideoxyadenosine, 2',3'-dideoxyinosine, 2',3'-dideoxythymidine, 2',3'-dideoxy-2',3'-didehydrothymidine and 2',3'-dideoxy2',3'-didehydrocytidine, immunomodulators such as interleukin-2 (IL-2) and granulocyte macrophage colony stimulating factor (GM-CSF), erythropoietin, ampligen, thymomodulin, thymopentin, foscarnet, ribavirin and inhibitors of HIV binding to CD4 receptors e.g., soluble CD4, CD4 fragments, CD4 hybrid molecules, glycosylation inhibitors such as 2-deoxy-D-glucose, castanospermine and 1-deoxynojirimycin.

The individual components of such combinations may be administered either sequentially or simultaneously in separate or combined pharmaceutical formulations.

When the compound (A) or a pharmaceutically acceptable derivative thereof is used in combination with a second therapeutic agent active against the same virus the dose of each compound may be either the same as or differ from that when the compound is used alone. Appropriate doses will be readily appreciated by those skilled in the art.

The compound (A) and its pharmaceutically acceptable derivatives may be prepared by any method known in the art for the preparation of compounds of analogous structure, for example as described in European Patent Publication 0382526 A2.

It will be appreciated by those skilled in the art that for certain of the methods described herein below the desired stereochemistry of the compound (A) may be obtained either by commencing with an optically pure starting material or by resolving the racemic mixture at any convenient stage in the synthesis. In the case of all the processes the optically pure desired product may be obtained by resolution of the end product of each reaction.

In one such process a 1,3-oxathiolane of formula (VIII)

(VIII)

wherein the anomeric group L is a displaceable group, is reacted with an appropriate base. Suitable groups L include —OR where R is an alkyl group, e.g., a $C_{1-6}$ alkyl group such as methyl or R is an acyl group, e.g., a $C_{1-6}$ alkyl group such as acetyl or halogen, for example iodine, bromine or chlorine.

The compound of formula (VIII) is conveniently reacted with 5-fluoro-cytosine or an appropriate pyrimidine base precursor thereof (previously silylated with a silylating agent such as hexamethyldisilazane) in a compatible solvent such as methylene chloride using a Lewis acid such as titanium tetrachloride, trimethylsilyltriflate, trimethylsilyl iodide (TMSI) or tin (IV) compound such as $SnCl_4$.

The 1,3-oxathiolanes of formula (VIII) may be prepared for example by reaction of an aldehyde of formula (VII) with a mercaptoacetal of formula (VI) in a compatible organic solvent, such as toluene in the presence of an acid catalyst for example a Lewis acid such as zinc chloride.

$HSCH_2CH(OC_2H_5)_2$ (VI)

$C_6H_5CO_2CH_2CHO$ (VII)

The mercaptoacetals of formula (VI) may be prepared by methods known in the art, for example G. Hesse and I. Jorder, *Chem. Ber.*, 85, pp. 924–932 (1952).

The aldehydes of formula (VII) may be prepared by methods known in the art for example E.G. Halloquist and H. Hibbert, *Can. J. Research*, 8, pp. 129–136 (1933). Conveniently the crude aldehyde (VII) may be purified by conversion to the crystalline bisulphite addition adduct and subsequent reconversion to the free aidehyde.

In a second process the compound (A) is obtained by base interconversion of a compound of formula (IX)

where B is a base convertible to 5-fluoro-cytosine. Such interconversion may be effected either by simple chemical transformation (e.g. the conversion of uracil base to cytosine) or by an enzymatic conversion using a deoxyribosyl transferase. Such methods and conditions for base interconversion are well known in the art of nucleoside chemistry.

In a third process a compound of formula (XI)

may be converted to the compound (A) by conversion of the anomeric $NH_2$ group to the 5-fluoro-cytosine base by methods well known in the nucleoside chemistry art.

Many of the reactions described hereinabove have been extensively reported in the context of nucleoside synthesis, for example in *Nucleoside Analogs-Chemistry, Biology and Medical Applications*, R. T. Walker et al., Eds., Plenum Press, New York (1979) at pages 165–192 and T. Ueda, *Chemistry of Nucleosides and Nucleotides*, Vol I, L.B. Townsend Ed., Plenum Press, New York (1988) at pages 165–192, the disclosures of which are incorporated by reference herein.

It will be appreciated that the above reactions may require the use of, or conveniently may be applied to, starting materials having protected functional groups, and deprotection might thus be required as an intermediate or final step to yield the desired compound. Protection and deprotection of functional groups may be effected using conventional means. Thus, for example, amino groups may be protected by a group selected from aralkyl (e.g. benzyl), acyl, aryl (e.g. 2,4-dinitrophenyl) or silyl; subsequent removal of the protecting group being effected when desired by hydrolysis or hydrogenolysis as appropriate using standard conditions. Hydroxyl groups may be protected using any conventional hydroxyl protecting group, for example, as described in *Protective Groups in Organic Chemistry*, J. F. W. McOmie, Ed., Plenum Press, New York (1973) or T. W. Greene, *Protected Groups in Organic Synthesis*, John Wiley and Sons, New York (1981). Examples of suitable hydroxyl protecting groups include groups selected from alkyl (e.g. methyl, t-butyl or methoxymethyl), aralkyl (e.g., benzyl, diphenylmethyl or triphenylmethyl), heterocyclic groups such as tetrahydropyranyl, acyl (e.g., acetyl or benzoyl) and silyl groups such as trialkylsilyl (e.g., t-butyldimethylsilyl). The hydroxyl protecting groups may be removed by conventional techniques. Thus, for example, alkyl, silyl, acyl and heterocyclic groups may be removed by solvolysis, e.g., by hydrolysis under acidic or basic conditions. Aralkyl groups such as triphenylmethyl may similarly be removed by solvolysis, e.g., by hydrolysis under acidic conditions. Aralkyl groups such as benzyl may be cleaved for example by treatment with $BF_3$/etherate and acetic anhydride followed by removal of acetate groups so formed at an appropriate stage in the synthesis. Silyl groups may also conveniently be removed using a source of fluoride ions such as tetra-n-butylammonium fluoride.

In the above processes compound (A) is generally obtained as a mixture of the cis and trans isomers of which the cis isomer is the compound of interest.

These isomers may be separated by physical means, e.g., chromatography on silica gel or by fractional crystallization, either directly or on a suitable derivative thereof, e.g., acetates (prepared for example with acetic anhydride) followed, after separate, by conversion back to the parent product (e.g., by deacetylation with methanolic ammonia).

Pharmaceutically acceptable salts of the compounds of the invention may be prepared as described in U.S. Pat. No. 4,383,114, the disclosure of which is incorporated by reference herein. Thus, for example, when it is desired to prepare an acid addition salt of compound (A) the product of any of the above procedures may be converted into a salt by treatment of the resulting free base with a suitable acid using convention methods. Pharmaceutically acceptable acid addition salts may be prepared by reacting the free base with an appropriate acid optionally in the presence of a suitable solvent such as an ester (e.g., ethyl acetate) or an alcohol (e.g., methanol, ethanol or isopropanol). Inorganic basic salts may be prepared by reacting the parent compound with a suitable base such as an alcohol (e.g., methanol). Pharmaceutically acceptable salts may also be prepared from other salts, including other pharmaceutical acceptable salts, of the compound (A) using conventional methods.

Compound (A) may be converted into a pharmaceutically acceptable phosphate or other ester by reaction with a phosphorylating agent, such as $POC_3$, or a suitable esterifying agent, such as an acid halide or anhydride, as appropriate. An ester or salt of compound (A) may be converted to the parent compound for example by hydrolysis.

Resolution of the final product, or an intermediate or starting material therefor may be effected by any suitable method known in the art: see for example E. L. Eliel, *Stereochemistry of Carbon Compounds*, McGraw Hill (1962) and S. H. Wilen, *Tables of Resolving Agents*.

Thus for example the compound (A) may be obtained by chiral HPLC using a suitable stationary phase for example acetylated β-cyclodextrin or cellulose triacetate and a suitable solvent for example an alcohol such as ethanol or an aqueous solution of for example triethyl ammonium acetate. Alternatively the compounds may be resolved by enzyme mediated enantioselective catabolism with a suitable enzyme such as cytidine deaminase or selective enzymatic degradation of a suitable derivative a 5'-nucleotidase. When resolution is effected enzymatically the enzyme may be employed either in solution or, more conveniently, in immobilized form. Enzymes may be immobilized by any method known in the art, for example by adsorption onto a resin such as Eupergit C.

The invention will be further described by the following examples which are not intended to limit the invention in any way. All temperatures are in degrees Celsius.

Intermediate 1

(±)-Cis-2-hydroxymethyl-5-(5'-fluorocytosin-1'-yl)1,3-oxathiolane (i) 2-Benzoyloxymethyl-5-acetoxy-1,3,oxathiolane Benzoyloxya. cetaldehyde (216.33 g, 1.32 mol) was dissolved in pyridine (373 ml, 4.61 mol) and 1,4-dithiane-2,5-diol (100.31 g, 0.66 mol) was added to the solution. The heterogenous mixture was stirred at 60°–65° C. under nitrogen atmosphere for 1 hour. At the end of the reaction, a complete solution was obtained. Dichloromethane (650 ml) was added to the reaction mixture and it was cooled to 0° C. with salt-ice bath. Acetyl chloride (281 ml, 3.95 mol) was added dropwise to the solution at 0–5° C. over 1.5–2 hours.

The reaction mixture was stirred at 0°–5° C. for 30 minutes, then it was poured carefully onto a cold (0°C.) solution of saturated sodium bicarbonate. The organic layer was separated. The water layer was extracted with dichloromethane (3×200 ml). The combined organic layers were washed with saturated sodium bicarbonate solution (3×200 ml) and brine (200 ml). The solution was dried over sodium sulfate and concentrated in vacuo. The traces of pyridine were removed by azeotropic distillation with benzene. 320.79 g crude product was obtained which was purified by Kugelrohr distillation or filtration through a short silica gel column. [Solvent system: hexane/ethyl acetate (3/1)].

(ii) Cis- and trans-2-benzgyloxymethvl-5-($N_4'$-acetyl-5'-fluoro-Cytosin-1'-yl)- 1,3-oxathiolane 5-Fluorocytosine (4.30 g, 33.3 mmol), hexamethyldisilazane (25 ml) and ammonium sulfate (120 mg) were boiled under reflux until the cytosine dissolved (3 hours) and then further refluxed for 2 hours. The hexamethyldisilazane was evaporated in vacuo and toluene (100 ml) was added to the residue to co-evaporate the solvents. The resulting solution bis(trimethylsilyl)-fluorocytosine in dichloromethane (40 ml) was added under argon to a solution of 2-benzoyloxymethyl-5-acetoxy-1,3-oxathiolane (8.537 g, 30.3 mmol) in dry dichloromethane (100 ml) and molecular sieves (4A, 2 g) previously prepared under argon and cooled at 0° C. for 20 minutes. [(Trifluoromethane-sulfonyl)oxy]trimethyl silane (6 ml, 31 mmol) was added to this mixture at 0° C. and the resulting solution was stirred at room temperature for 2 hours. The filtrate was shaken two times with 300 ml of brine and one time with distilled water. The organic layer was dried over magnesium sulfate, filtered and evaporated to dryness. This afforded a crude 5-fluoro-cytosine derivative (10.1 g). $R_f$=0.57 (EtOAC:MeOH 9:1).

This residue was acetylated in the next step without further purification. The crude material was dissolved in dry dichloromethane (120 ml) in a 500 ml round bottom flask under argon. Triethylamine (12.7 ml, 91.1 mmol) and dimethyl aminopyridine (111 mg, 0.9 mmol) were added to the solution. The flask was then immersed in an ice bath for 1 hour under argon. Acetic anhydride (4.3 ml, 45 mmol), distilled over sodium acetate, was syringed into the cooled flask. The mixture was stirred overnight and then carefully decanted into an erlenmeyer flask containing saturated sodium bicarbonate solution. The product was then washed with distilled water followed by brine solution. The methylene chloride portions were dried and evaporated under high vacuum to dryness, yielding an acetylated α/β mixture as a colorless foam, weighing 9.6 g after drying. Flash chromatography of this material using ethylacetate: methanol (9:1) afforded 3.1 g, 7.8 mmol (46%) pure trans- and 3.5 g, 8.9 mmol (30%) pure cis- title compounds.

trans-isomer: $R_f$=0.65 in ethyl acetate:methanol 9:1
U.V.: (MeOH) Lambda max: 309 nm
$^1$H-NMR δ (ppm in CDCL$_3$) 8.77 (b, 1H; C$_4'$—NH—Ac) 8.06 (m, 2H; aromatic) 7.70 (d, 1H; C$_6'$—H, $J_{CF}$= 6.3 Hz) 7.62 (m, 1H; aromatic) 7.49 (m, 2H; aromatic) 6.51 (dd, 1H; C$_5$—H) 5.91 (dd, 1H; C$_2$—H) 4.48 (dd, 2H; C$_2$—CH$_2$OCOC$_6$H$_5$ ) 3.66 (dd, 1H; C$_4$—H) 3.34 (dd, 1H; C$_4$—H) 2.56 (s, 3H; NH-COCH$_3$)

cis-isomer: $R_f$=0.58 in ethyl acetate:methanol 9:1
U.V.: (MeOH) Lambda max: 309 nm
$^1$H-NMR δ (ppm in CDCl$_3$) 8.72 (b, 1H; C$_4'$—NH—Ac) 8.06 (m, 2H; aromatic) 7.87 (d, 1H; C$_6'$—H, $J_{CF}$= 6.2 Hz) 7.60 (m, 1H; aromatic) 7.49 (m, 2H; aromatic) 6.32 (dd, 1H; C$_5$—H) 5.47 (dd, 1H; C$_2$—H) 4.73 (dd, 2H; C$_2$—CH$_2$OCOC$_6$H$_5$) 3.62 (dd, 1H; C$_4$—H) 3.19 (dd, 1H; (C$_4$—H) 2.55 (s, 3H; NH; —COCH$_3$)

(iii) (±)-Cis-hydroymethyl-5-(5'-fluorocytosin-1'-yl)1,3-oxathiolane 1.2 g (3.35 mmol) of cis-2-benzoyloxymethyl-5- ($N_4'$-acetyl-5'-fluorocytosin-1'-yl)-1,3-oxathiolane was stirred in 30 ml of methanolic ammonia at 0° C. for 1 hour and then overnight at room temperature. The mixture was evaporated under reduced pressure. The residue was triturated twice (2×30 ml) with anhydrous ether. The solid residue was recrystallized in absolute ethanol to give 655 mg (2.64 mmol, 87%) of pure cis title product: m.p. 204°–206° C.; $R_f$=0.21 in ethylacetate:methanol (9:1). The desired compound was identified by $^1$H, $^{13}$C-NMR and U.V. Lambda max (H$_2$O) 280.9 nm.

cis-isomer:
$^1$H-NMR δ (ppm in DMSO-d$_6$) 8.22 (d, 1H; C$_6'$—H, $J_{CF}$=7.26 Hz) 7.84 (d, 2H; C$_4'$—NH$_2$) 6.16 (t, 1H; C$_5$—H) 5.43 (t, 1H; C$_2$—CH$_2$—OH) 5.19 (t, 1H; C$_2$—H) 3.77 (m, 2H; C$_2$—CH$_2$OH) 3.35 (dd, 1H; C$_4$—H) $^{13}$C-NMR (DMSO-d$_6$)

| C$_6'$ | C$_2'$ | C$_4'$ | C$_5'$ |
| --- | --- | --- | --- |
| 153.46 | 158.14 | 134.63 | 126.32 |
|  | ($^2J_{CF}$ = 14.0 Hz) | (J$_{CF}$ = 24.1 Hz) | (J$_{CF}$ = 32.5 Hz) |
| C$_5$ | C$_4$ | C$_2$ | CH$_2$OH |
| 86.82 | 36.80 | 86.77 | 62.32 |

EXAMPLE 1

(−)- 4-Amino-5-floro-1-(2-hydroxymethyl-1,3-oxathiolan-5-yl)-(1H)-pyrimidin-2-one (i) (±) Cis-2-hydroxymethyl5-(5'-fluorocytosin-1'-yl)-1,3-oxathiolane monophosphate To a stirred mixture of Intermediate 1 (500 mg, 2.024 mmol) in dry trimethyl phosphate (10 ml) cooled to 0° C., was added dropwise phosphorus oxychloride (1.22 ml, 13.1 mmol). The reaction mixture was stirred at that temperature for 1 hour and then quenched in ice water. The pH of the cold mixture was adjusted to 3 by the addition of aqueous 1N sodium hydroxide, then applied to a charcoal column (5 g, DARCO), which was eluted with water followed by ethanol and aqueous ammonia in a (10:10:1) ratio. Fractions containing crude monophosphate were combined and evaporated and subsequently was applied to a column containing 15 g of DEAE sephadex A25 (HCO$_3$-form). Elution was undertaken with a gradient of water (300 ml), 0.1M-NH$_4$HCO$_3$ (300 ml ), and 0.2M NH$_4$HCO$_3$ (100 ml). Evaporation of appropriate fractions after dilution with water (30 ml ) afforded (±) cis-2-hydroxymethyl-5(5'-fluorocytosin-1'-yl)-1,3-oxathiolane monophosphate as a white solid $R_f$=0.5 (n. PrOH:NH$_4$OH 6:4) yield=612 mg, 1.77 mmol, 87.9%. $^1$H NMR δ (ppm in D$_2$O). 8.27 (d, 1H, C$_6'$—H, $J_{H-F}$=6.4 Hz), 6.33 (dd, 1H, C$_5$—H), 5.47 (t, 1H, C$_2$—H), 4.84 (m, $_2$H, C$_2$-CH$_2$OH), 3.63 (dd, 1H, C$_4$H), 3.30 (dd, 1H, C$_4$H). HPLC>99%.

(ii) (±)-Cis-2-hydroxymethyl-5-(5'-flurocytosin-1'-yl)-1,3-oxathiolane

To a solution of (±) cis-2-hydroxymethyl-5(5'-fluorocytosin-1'-yl)-1,3-oxathiolane monophosphate (100 mg, 0.29 mmol) in 3 ml of glycine buffer solution [glycine (52.6 mg) and magnesium chloride (19 mg) in water (10 ml)], was added in one portion 5'-nucleotidase [Sigma, 3.5 mg at 29 unit/mg]. The resulting mixture was incubated at 37° C. with shaking. The reaction was monitored by HPLC [chiral column α-acid glycoprotein (AGP) using 0.2M sodium phosphate as eluant at pH 7 with a flow rate 0.15 ml/min] at different intervals. Only the (+)-enantiomer was observed after 2.5 hours. More enzyme (2 mg) was added, and incubation was continued for a further 3 hours. HPLC analysis clearly showed selective and complete hydrolysis of the (+)-enantiomer. The resulting mixture was applied to a column of DEAE sephadex A-25 ($HCO_3$ form). Elution was undertaken with water (155 ml), followed by 0.1 and 0.2M $NH_4HCO_3$ (100 ml each). Appropriate fractions containing the first eluted nucleoside were combined and concentrated. The remaining solid was purified on a short column silica using ethyl acetate, methanol (4.5:0.5) as eluant and then separated by HPLC (employing the above mentioned conditions ). This afforded pure (+)-cis-2-hydroxymethyl-5-(5'-fluorocytosin-1'-yl ) -1,3-oxathiolane (23 mg, 0.093 mmol, 32%) as a white solid $(\delta)^{21}{}_s$+123° C. [c, 1.00, MeOH]m.p. 185° C. NMR δ (ppm in DMSO). 8.26 (d, 1H, $C'_6$—H, $J_{H\text{-}F}$=5.22 Hz), 7.87 (s, 1H, $NH_2$, $D_2O$ exchangeable;), 7.63 (s, 1H, $NH_2O$, $D_2O$ exchangeable), 6.20 (dd, 1H, $C_{5\_}H$), 5.48 (t, 1H, $C_2H$), 5.24 (t, 1H, $CH_2$—OH, $D_2O$ exchange), 3.84 (m, 2H, $C_2$—$CH_2OH$), 3.50 (dd, 1H, $C_4H$), 3.37 (dd, 1H, $C_4H$).

(iii) (−)-Cis-2-hydroxymethyl-5-(5'-fluorocytosin-1'-yl)-1,3-oxathiolane

Appropriate fractions from the sephadex column containing the second eluted nucleoside described in step (ii) were combined and evaporated under reduced pressure. The residue was dissolved in 2 ml of water and treated with alkaline phosphatase (Sigma, 1 ml at 60 units/ml) followed by incubation at 37° C. for 1.5 hours. Solvent was then evaporated and the residue was purified by column chromatography on silica gel using EtOAc:MeOH (4:1) as eluent followed by HPLC (separation using the same conditions mentioned above). This afforded pure (−)-cis-2-hydroxymethyl-5(5'-fluorocytosin-1'-yl)-1,3-oxathiolane (20 mg, 0.081 mmol, 28%) m.p. 190° C. (d) rf=0.21, EtOAc:MeOH (4:1). U.V.: ($H_2O$) max: 279.1nm. $^1$H NMR δ (ppm in DMSO-$d_6$), 8.25 (d, 1H, $C'_6$—H, $J_{HF}$=7.26 Hz), 7.88 (b, 1H, $C'_4$—$NH_2$, $D_2$ O exchangeable), 7.85 (b, 1H, $C'_4$—$NH_2$: $D_2O$ exchangeable), 5.24 (t, 1H, $C_2$—H), 3.83 (m, 2H, $C_2$—$C_2$—$CH_2$—OH), 3.19 (dd, 1H, ($C_4$—H), 3.15 (dd, 1H, $C_4$ . H).

Intermediate 2 and Example 2 depict an alternate process for preparing the compound of formula (A).

Intermediate 2

(1'R,2'S,5'R)-MENTHYL-5R-(5'-FLUOROCYTOSING-1"-YL)-1,3-OXATHIOLANE-2S-CARBOXYLATE

To a suspension of 5-fluorocytosine (155 mg, 1.2 mmol) in $CH_2Cl_2$ (1 mL) at room temperature under an argon atmosphere was added, success ively, 2,4,6-collidine (0. 317 mL, 2.4 mmol) and t-butyldimethylsilyl trifluoromethanesulfonate (0. 551 mL, 2.4 mmol). The resultant mixture was stirred for 15 minutes and a clear solution was obtained. A solution of (1'R,2'S,5'R)-mentlyl-5R-acetoxy-1,3-oxathiolane-2S-carboxylate (330 mg, 1 mmol) in $CH_2Cl_2$ (0.5 mL) was introduced, followed by iodotrimethysilane (0.156 mL, 1.1 mmol). Stirring was continued for 3 hours. The mixture was diluted with $CH_2Cl_2$ (20 mL) and washed successively with saturated aqueous $NaHSO_3$, water, brine and then was concentrated. The residue was taken up in ether-hexanes (1:1, 10mL) and saturated aqueous $NaHCO_3$ (2 mL) and stirred at room temperature for 15 minutes. The aqueous layer was removed and the organic phase was centrifuged to afford a white solid which was washed with hexanes (3×5 mL) and then dried under vacuum. The product (1'R,2'S, 5'R)-menthyl-5R-(5"fluorocytos in-1"yl)-1,3-oxathiolane-2S-carboxylate (350 mg, 88% ) thus obtained contained about 6% of (1'R,2'S,5'R)-menthyl5S-(5"-fluorocytosin-1"-yl)-1,3-oxathiolane-2S-carboxylate (NMR). This material was recrystallized from MeOH/$CH_2Cl_2$/benzene to give a crystalline product: $[\alpha]_D^{26}$+22. (c, 0 19, MeOH); m.p 216°–218° C., $^1$H NMR (CDCl$_3$) δ 0.78 (d, 3H, J=7 Hz), 0.91 (t, 6H, J=7.3 Hz), 1.00 (m, 2H), 1.39–2.04 (m, 7H), 3.12 (dd, 1H, J=6.6 Hz, 6.1 Hz), 3.52 (dd, 1H, J=4.7 Hz, 6.1 Hz), 4.79 (dt, 1H, J=4.4 Hz, 4.3 Hz), 5.46 (S, 1 H), 5.75 (bs, 1H, exchangeable), 6.42 (5t, 1H, J=5.0 Hz), 8.10 (bs, 1H, exchangeable), 8.48 (d, 1H, J=6.6 Hz); $^{13}$C NMR (CDCl$_3$-DMSO-$d_6$): δ6 16.7, 21.2, 22.4, 23.7, 26.6, 31.8, 34.4, 36.6, 40.5, 47.2, 77.1, 79.1, 90.8, 126.3 (d, J=33 Hz), 137.1 (d, J=244 Hz), 154.2, 158.3 (d, J=15 Hz), 170.1.

EXAMPLE 2

2S-HYDROXYMETHYL-5R-(5'-FLUOROCYTOSIN-1'-YL)-1.3 -OXATHIOLANE

To a suspension of lithium aluminum hydride (10 rag, 0.54 mmol) in THF (1 mL) at ambient temperature under an argon atmosphere was slowly added a solution of (1'R,2'S, 5'R)-menthyl-5R-(5"-fluorocytosinyl) 1,3 -oxathiolane-2S-carboxylate (54 mg, 0.135 mmol ) in THF (2 mL). The reaction mixture was allowed to stir for 30 minutes, then quenched with excess methanol (2 mL), followed by the addition of silica gel (3 g) . The resultant slurry was subjected to silica gel column chromatography (EtOAc-Hexane-MeOH, 1:1:1) to provide a gummy solid which was dried azeotropically with toluene to give 20.7 mg (63%) of a white solid as the product: $[\alpha]_D^{26}$+114. (C, 0.12, MeOH); $^1$H NMR (DMSO-d6) δ3.14 (dd, 1H, J=4.3, 11.9 Hz), 3.42 (dd, 1H J=5.3, 11.9 Hz), 3.76 (m,2H), 5.18 (m, 1H), 5.42 (t, 1H, J=4.8 Hz), 6.14 (m, 1H), 7.59 (br m, 1H, exchangeable), 7.83 (br m, 1H exchangeable), 8.20 (d, 1H, J=7.66 Hz).

EXAMPLE 3

Bioloqical Activity (i) Antiviral Activity

Antiviral activity of the compound of Example 1 was determined against HIV-1 in the following cell lines.

C8166 cells, a human T-lymphoblastoid cell line, infected with HIV-1 strain RF.

MT-4 cells, a human T-cell leukaemia cell line, infected with HIV-1 strain RF.

Antiviral activity in C8166 cells was determined by inhibition of syncytium formation (Tochikura et al Virology, 164, 542–546) and in MT-4 cells by inhibition of formazan conversion [Baba et al, Biochem Biophys Res Commun., 142, pp. 128–134 (1987); Mossman, J. Immun. Meth., 65, pp. 55–57 (1983)]. Antiviral activities were also determined by analyzing the amount of HIV p24 antigen synthesized in the presence and absence of enantiomers.

The results are shown in Tables 1 and 2 below:

TABLE 1

| 50% Antiviral Activity (μg/ml) | | |
| --- | --- | --- |
| Assay | Formazan | Inhibition of syncytium formation |
| Cells | MT-4 | C8166 |
| Virus (HIV-1) | HIV-1 RF | HIV-1 RF |
| (+)-enantiomer | >1 | 0.04 |
| (−)-enantiomer | 0.14 | 0.0018 |
| Intermediate 1 | 0.065 | 0.013 |
| AZT | | 0.0038 |

TABLE 2

| 50% Inhibition HIV p24 Synthesis (μg/ml) | |
| --- | --- |
| Cells | C8166 |
| Virus | RF |
| (+)-enantiomer | 0.1 |
| (−)-enantiomer | 0.0022 |
| Intermediate 1 | 0.011 |
| AZT | 0.017 |

(ii) Cytotoxicity

The cytotoxicities of the compounds of Example 1 and the racemic compound (Intermediate 1) were determined in two CD4 cell lines: H9 and CEM.

Compounds for test were serially diluted from 100 μg/ml to 0.3 μg/ml (final concentrations) in 96 well microtitre plates. $3.6 \times 10^4$ cells were inoculated into each well of the plates including drug-free controls. After incubation at 37° C. for 5 days, the viable cell count was determined by removing a sample of cell suspension and counting trypan blue excluding cells in a hemocytometer.

The results are shown in Table 3.

TABLE 3

| | 50% Cytotoxicity (μg/ml) | |
| --- | --- | --- |
| Compound | CEM cells | H9 cells |
| (+)-enantiomer | 217 | 334 |
| (−)-enantiomer | 148 | 296 |
| Intermediate 1 | 173 | 232 |

I claim:

1. (−)-Cis-4-amino-5-fluoro-1-(2-hydroxymethyl-1,3-oxathiolan- 5-yl)-(1H)-pyrimidin-2-one or a pharmaceutically acceptable salt, ester or salt of an ester thereof.

2. The substantially pure (−)-enantiomer of cis-4-amino-5-fluoro-1-(2-hydroxymethyl-1,3-oxathiolan-5-yl)-(1H)-pyrimidin-2-one or a pharmaceutically acceptable salt, ester or salt of an ester thereof, wherein the (+) enantiomer is present in an amount of no more than 5% w/w.

3. The compound of claim 2 wherein the (+)-enantiomer is present in an amount of no more than about 2% w/w.

4. The compound of claim 2 wherein the (+)-enantiomer is present in an amount of less than about 1% w/w.

5. A pharmaceutical composition comprising a compound as in any one of claims 1, 2, 3, or 4 in combination with a pharmaceutically acceptable carrier.

* * * * *

UNITED STATES PATENT AND TRADEMARK OFFICE
CERTIFICATE OF CORRECTION

PATENT NO. : 5,538,975
DATED : July 23 1996
INVENTOR(S) : Dionne, G.

It is certified that error appears in the above-indentified patent and that said Letters Patent is hereby corrected as shown below:

<u>Column, Line</u>

| | |
|---|---|
| column 1, line 48 | where "phazmaceutically" should read -- pharmaceutically -- ; |
| column 2, line 4 | where "However.," should read -- However, -- ; |
| column 2, line 18 | where "methoxymethylL" should read -- methoxymethyl -- ; |
| column 2, line 66 | where "vital" should read -- viral --; |
| column 3, line 2 | where "Mount" should read -- amount -- ; |
| column 3, line 11 | where "a" should read -- as --; |
| column 3, line 54 | where "boltus" should read -- bolus -- ; |
| column 3, line 64 | where "pharmaceutically" should read -- pharmaceutical -- ; |
| column 4, line 19 | where "tables" should read -- tablets -- ; |
| column 5, lines 52-53 | where "phazmaceutically" should read -- pharmaceutically -- ; |

UNITED STATES PATENT AND TRADEMARK OFFICE
CERTIFICATE OF CORRECTION

PATENT NO. : 5,538,975  
DATED : July 23 1996  
INVENTOR(S) : Dionne, G.

Page 2 of 6

It is certified that error appears in the above-indentified patent and that said Letters Patent is hereby corrected as shown below:

Column, Line

| | |
|---|---|
| column 5, lines 62-63 | where "2',3'-dideoxy2'3'-didehydrocytidine" should read -- 2',3'-dideoxy-2',3'-didehydrocytidine -- ; |
| column 6, line 67 | where "aidehyde" should read -- aldehyde -- ; |
| column 7, line 30 | where "165-192" shuld read -- 1-112 -- ; |
| column 8, line 2 | where "chromatcgraphy" should read -- chromatography -- ; |
| column 8, line 5 | where "separate," should read -- separation -- ; |
| column 8, line 22 | where "pharmaceutical" should read -- pharmaceutically -- ; |
| column 8, line 26 | where "POC$_3$" should read -- POCl$_3$ -- ; |
| column 8, line 43 | where "derivative a" should read -- derivative using a -- ; |
| column 8, line 59 | where "Benzoyloxya. cetaldehyde" should read -- Benzoyloxyacetaldehyde -- ; |
| column 9, line 13 | where "benzgyloxymethyvl" should read -- benzoyloxymethyl -- ; |

UNITED STATES PATENT AND TRADEMARK OFFICE
CERTIFICATE OF CORRECTION

PATENT NO. : 5,538,975
DATED : July 23 1996
INVENTOR(S) : Dionne, G.

It is certified that error appears in the above-indentified patent and that said Letters Patent is hereby corrected as shown below:

Column, Line

| | |
|---|---|
| column 9, line 14 | where fluoro-Cytosin" should read -- fluoro-cytosin -- ; |
| column 9, line 67 | where the semicolon ";" after "NH" should be deleted; |
| column 10, line 1 | where "(±)-Cis-hydroymethyl" should read -- (±)-Cis-hydroxymethyl -- ; |
| column 10, line 1 | where a hyphen -- - -- should be inserted between "(5'-fluorocytosin-1'-yl)" and "1,3-oxathiolane"; |
| column 10, line 3 | where "3.35" should read -- 3.05 -- ; |
| column 10, line 32 | where "floro" should read -- fluoro -- ; |
| column 10, line 35 | where "hydroxymethyl5" should read -- hydroxymethyl-5 -- ; |
| column 10, line 47 | where "was" should read -- were -- ; |
| column 10, line 52 | where a hyphen -- - -- should be inserted between "5" and "(5'-"; |
| column 10, line 56 | where "6.4" should read -- 6.47 -- ; |
| column 10, line 57 | where "$_2$H" should read -- 2H -- ; |

UNITED STATES PATENT AND TRADEMARK OFFICE
CERTIFICATE OF CORRECTION

PATENT NO. : 5,538,975
DATED : July 23 1996
INVENTOR(S) : Dionne, G.

It is certified that error appears in the above-indentified patent and that said Letters Patent is hereby corrected as shown below:

Column, Line

| | |
|---|---|
| column 10, line 59 | where "($\pm$)" should read -- (+) --; |
| column 10, line 59 | where "flurocytosin" should read -- fluorocytosin -- ; |
| column 10, line 61 | where a hyphen -- - -- should be inserted between "5" and "(5'-"; |
| column 11, line 19 | where the semicolon ";" after "exchangeable" should be deleted; |
| column 11, line 20 | where "NH$_2$O" should read -- NH$_2$ --; |
| column 11, line 21 | where "exchange" should read -- exchangeable -- ; |
| column 11, line 24 | where "fluorocvtosin" should read -- fluorocytosin -- ; |
| column 11, line 36 | where a hyphen -- - -- should be inserted between "5" and "(5'-"; |
| column 11, line 40 | where the extra space " " between "D$_2$" and "O" should be deleted; |
| column 11, line 42 | where "C$_2$-C$_2$-C$\underline{H}_2$-OH" should read -- C$_2$-C$\underline{H}_2$-OH -- ; |
| column 11, line 42 | where the open parentheses "(" before "C$_4$" should be deleted; |

UNITED STATES PATENT AND TRADEMARK OFFICE
CERTIFICATE OF CORRECTION

PATENT NO. : 5,538,975
DATED : July 23 1996
INVENTOR(S) : Dionne, G.

Page 5 of 6

It is certified that error appears in the above-indentified patent and that said Letters Patent is hereby corrected as shown below:

<u>Column, Line</u>

| | |
|---|---|
| column 11, line 43 | where "$C_4$ . H" should read -- $C_4$-H -- ; |
| column 11, line 50 | where "FLUOROCYTOSING" should read -- FLUOROCYTOSIN -- ; |
| column 11, line 55 | where "success ively" should read -- successively -- ; |
| column 11, line 59 | where "mentlyl" should read -- menthyl -- ; |
| column 12, line 4 | where "fluorocytos in" should read -- fluorocytosin -- ; |
| column 12, line 6 | where "methyl5S" should read -- methyl-5S -- ; |
| column 12, line 9 | where "22." should read -- 22° -- ; |
| column 12, line 9 | where "0 19" should read -- 0.19 -- ; |
| column 12, line 9 | where "m.p" should read -- m.p. -- ; |
| column 12, line 17 | where "δ6 16.7" should read -- δ 16.7 -- ; |
| column 12, line 26 | where "1.3-OXATHIOLANE" should read -- 1,3-OXATHIOLANE -- ; |
| column 12, line 28 | where "rag" should read -- mg -- ; |

UNITED STATES PATENT AND TRADEMARK OFFICE
CERTIFICATE OF CORRECTION

PATENT NO. : 5,538,975
DATED : July 23 1996
INVENTOR(S) : Dionne, G.

It is certified that error appears in the above-indentified patent and that said Letters Patent is hereby corrected as shown below:

<u>Column, Line</u> column 12, line 31      where "fluorocytosinyl" should read -- fluorocytosin-1″-yl -- ;

column 12, line 31      where a hyphen -- - -- should be inserted between ")" and "1,3" and the extra space " " between "1,3" and "-oxathiolane" should be deleted;

column 12, line 40      where "114. (C" should read --114° (c -- ;

column 12, line 42      where a comma -- , -- should be inserted after "1H";

column 12, line 44      where a comma -- , -- should be inserted after the first "1H".

column 12, line 50      where "Bioloquical" should read -- Biological -- ;

Signed and Sealed this

Third Day of December, 1996

Attest:

BRUCE LEHMAN

Attesting Officer      Commissioner of Patents and Trademarks